(12) United States Patent
Morisawa et al.

(10) Patent No.: US 6,472,547 B1
(45) Date of Patent: Oct. 29, 2002

(54) PROCESS FOR PRODUCING BISMUTH TERTIARY AMYLOXIDE

(75) Inventors: Satoru Morisawa, Saitama (JP); Masamichi Matsumoto, Kumagaya (JP); Hidekimi Kadokura, Tokyo (JP)

(73) Assignee: Kabushikikaisha Kojundokagaku Kenyusho, Saitama (JP)

( * ) Notice: Subject to any disclaimer, the term of this patent is extended or adjusted under 35 U.S.C. 154(b) by 0 days.

(21) Appl. No.: 10/080,792

(22) Filed: Feb. 20, 2002

(30) Foreign Application Priority Data

Mar. 5, 2001 (JP) .......................................... 2001-110629

(51) Int. Cl.[7] .................................................. C07F 9/94
(52) U.S. Cl. ........................ 556/76; 106/479; 427/248.1
(58) Field of Search ........................... 556/76; 106/479; 427/248.1

(56) References Cited

U.S. PATENT DOCUMENTS 6,355,821 B1 * 3/2002 Koplick et al. ............... 556/57

OTHER PUBLICATIONS

Matchett et al., Inorganic Chemistry, vol. 29, No. 3, pp. 358–360 (1990).*

Massiani et al., Polyhedron, vol. 10, No. 4, pp. 437–445 (1991).*

* cited by examiner

Primary Examiner—Porfirio Nazario-Gonzalez
(74) Attorney, Agent, or Firm—Fattibene & Fattibene; Paul A. Fattibene; Arthur T. Fattibene

(57) ABSTRACT

This invention provides a process for producing bismuth tertiary amyloxide which is a starting material for forming a ferroelectric film such as $SrBi_2Ta_2O_9$ containing bismuth oxide, or an oxide superconductive film such as $Bi_2Sr_2CaCu_2O_8$, by the CVD method or sol-gel method. This process comprises reacting bismuth bromide with sodium tertiary amyloxide or potassium tertiaryamyloxide in a toluene solvent containing 5 to 30 weight % tetrahydrofuran, then separating a byproduct sodium bromide or potassium bromide by filtration and recovering bismuth tertiary amyloxide by distillation under reduced pressure.

2 Claims, No Drawings

PROCESS FOR PRODUCING BISMUTH TERTIARY AMYLOXIDE

BACKGROUND OF THE INVENTION

1. Field of the Invention

This invention relates to a process for producing bismuth tertiary amyloxide useful for producing composite oxides containing bismuth oxide in the CVD method, sol-gel method etc.

2. Description of the Prior Art

Bismuth layered composite oxides are useful as ferroelectrics such as $SrBi_2Ta_2O_9$ and $Bi_4Ti_3O_{12}$ and superconductors such as $Bi_2Sr_2CaCu_2O_8$. As the starting material for producing such film by the CVD method or sol-gel method, bismuth alkoxides or bismuth tris-β-diketonates have been examined. These compounds should have high purity so as not to contain any alkali metals such as sodium and potassium. Out of many bismuth alkoxides, those which can be refined to high degrees substantially using sublimation and distillation are only bismuth tertiary butoxide (referred to hereinafter as $Bi(OtBu)_3$) and bismuth tertiary amyloxide (referred to hereinafter as Bi $(OtAm)_3$). Because these compounds are tertiary alkoxides, the exchange reaction thereof with other alcohols or β-diketones is easy, and can serve as the starting material for a large number of useful bismuth alkoxides and bismuth β-diketonates.

For refining or mass production, distillation is generally more preferable than sublimation. Since the melting point of $Bi(OtBu)_3$ is as high as 150° C., it will be pyrolyzed if distilled at the melting point or more. Accordingly, $Bi(OtBu)_3$ must be refined by sublimation, but efficiency is deteriorated. On the other hand, $Bi(OtAm)_3$ has a melting point of 90° C., and can be refined by distillation. Accordingly, there was demand for a process for producing a highly purified product of $Bi(OtAm)_3$.

M. A. Matchett, M. Y. Chiang and W. E. Buhro, in Inorg. Chem. Vol.29,360 (1990), have disclosed a process for producing $Bi(OtAm)_3$, which comprises reacting dimethylaminobismuth $Bi(N(CH_3)_2)_3$ with tertiary amyl alcohol $HOC(CH_3)_2C_2H_5$ (referred to hereinafter as tAmOH) and then recovering the product in at least 90% yield by sublimation. Certainly, this prior art process is a process for producing high-purity $Bi(OtAm)_3$. However, there is the problem that the yield of the starting material $Bi(N(CH_3)_2)_3$, which is produced by reacting bismuth chloride with dimethylaminolithium, is as low as up to 50%. Further, $Bi(N(CH_3)_2)_3$ is spontaneously flammable, is poor in thermal stability, and problematic in storage etc., and thus it is not preferable as the starting material for mass production of $Bi(OtAm)_3$.

M. C. Massiani et al., in Polyhedron Vol. 10,437 (1991), have disclosed that a solution of sodium tertiary butoxide in tetrahydrofuran (referred to hereinafter as THF) is reacted with a solution of bismuth bromide in THF, whereby 3.1 g of $Bi(OtBu)_3$ is recovered in 80% yield by sublimation. However, M. C. Massiani et al. do not refer to $Bi(OtAm)_3$. Further, they do not refer to the purity of the resulting $Bi(OtBu)_3$. Nor do they refer to a method of removing sodium bromide (NaBr) produced as a byproduct.

In the case of mass production, the removal of NaBr produced as a byproduct constitutes an important procedure. When the amount of NaBr is small, $Bi(OtBu)_3$ can be recovered by sublimation directly from the NaBr-containing product, but when its amount is large, recovery is difficult.

As can be seen from the foregoing description, there was no process suitable for mass production of $Bi(OtAm)_3$.

The present inventors attempted application of the production process of M. C. Massiani et al. to production of $Bi(OtAm)_3$. A solution of sodium tertiary amyloxide (referred to hereinafter as NaOtAm) in THF was reacted with a solution of $BiBr_3$ in THF, and crystals of NaBr produced as a byproduct were attempted to be separated by filtration through filter paper No. 131, but the fine crystals passed through the filter paper, and thus a transparent filtrate could not be obtained. Even if conditions such as reaction temperature, aging time, stirring rate etc. were changed, good results could not be obtained. In the pure THF solvent, particles of crystalline NaBr did not grow to be filtered off.

Further, the present inventors found the problem of discoloration; that is, colorless $Bi(OtAm)_3$ rapidly turns violet due to an unknown reason, possibly because the pure THF solvent acts strongly on $Bi(OtAm)_3$ or because THF can contain oxygen or water dissolved therein. From these results, it was found that the use of pure THF as the solvent in the process has problems such as difficult separation of the byproduct NaBr by filtration and easy deterioration of $Bi(OtAm)_3$.

SUMMARY OF THE INVENTION

The object of this invention is to provide a process suitable for mass production of $Bi(OtAm)_3$, to further provide a process of facilitating separation of crystals of a byproduct NaBr or KBr, or NaCl or KCl, through filtration after reacting NaOtAm or KOtAm with $BiBr_3$ or $BiCl_3$, and to further provide a process with less deterioration of $Bi(OtAm)_3$.

According to one aspect of this invention, there is provided a process for producing bismuth tertiary amyloxide, which comprises reacting bismuth bromide or bismuth chloride with sodium tertiary amyloxide or potassium tertiary amyloxide in an organic solvent containing tetrahydrofuran, then separating a byproduct sodium bromide or potassium bromide, or sodium chloride or potassium chloride, by filtration and recovering bismuth tertiary amyloxide by distillation under reduced pressure.

According to another aspect of this invention, there is provided a process for producing bismuth tertiary amyloxide, wherein the organic solvent containing tetrahydrofuran is a toluene solution containing 5 to 30 weight % tetrahydrofuran.

DETAILED DESCRIPTION OF THE INVENTION

In the basic reaction of this invention, the process for producing $Bi(OtBu)_3$, as disclosed by M. C. Massiani et al., has been applied to production of $Bi(OtAm)_3$, and this reaction is expressed by each of the following two reactions:

$BiBr_3$ (or $BiCl_3$)+3NaOtAm→$Bi(OtAm)_3$+3NaBr (or 3NaCl)  (1)

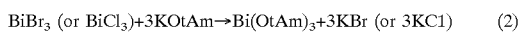

$BiBr_3$ (or $BiCl_3$)+3KOtAm→$Bi(OtAm)_3$+3KBr (or 3KCl)  (2)

Hereinafter, the invention is described by reference to the process where NaOtAm was used.

This reaction is conducted in an organic solvent containing THF. The organic solvent is preferably an aromatic hydrocarbon, particularly preferably toluene. Hereinafter, the reaction using a THF-containing toluene solution is described.

The solvent is a mixed solvent consisting of a solvent for dissolving or suspending $BiBr_3$ and a solvent for dissolving or suspending NaOtAm. The weight % of THF in the THF-containing toluene solution in this invention is defined as follows:

THF weight %={THF weight/(THF weight+toluene weight)}×100 (%)

This is indicative of the weight % of THF in the mixed solvent just after the reaction is finished, in other words, in the mixed solvent to be subjected to the filtration step.

In this invention, the THF-containing toluene solution is preferably toluene containing 5 to 30 weight % THF. If the content of THF is less than 5 weight %, $BiBr_3$ and NaOtAm are hardly dissolved thus resulting in a reduction in the rate of reaction. On the other hand, when the content exceeds 30weight %, NaBr produced as a byproduct hardly grows as crystals, thus making separation thereof by filtration difficult. Further, $Bi(OtAm)_3$ is deteriorated in the same degree as in pure THF, and therefore a content of THF outside of the above-defined range is not preferable.

The starting material NaOtAm is obtained by reacting Na with an excess of tAmOH at 100 to 130° C. After unreacted tAmOH is distilled away, the remaining NaOtAm is dried and then dissolved in a THF-containing toluene solution.

Anhydrous $BiBr_3$ or $BiCl_3$, which is equimolar to the above NaOtAm, is dissolved in a THF-containing solution and then added dropwise to while being stirred, and reacted with, the THF-containing toluene solution of NaOtAm. The reaction temperature is 30 to 60° C., and the reaction time is 0.5 to 5 hours or so. Then, the reaction mixture is aged by stirring it at 80° C. for 6 hours.

The reaction mixture is cooled to room temperature and then filtered. This filtration is conducted in nitrogen or argon free of oxygen or humidity. The filtration method makes use of filtration under reduced pressure, filtration under pressure, centrifugal filtration etc. In the case of filtration under reduced pressure, filter paper NO. 131 (3 μm pores) can be used to obtain a transparent filtrate. From the filtrate, the solvent is distilled away at 80° C. at a pressure of 1 Torr, and then the residue is charged into a still pot where it is distilled at 120° C. at a pressure of 1 Torr, to give white $Bi(OtAm)_3$ crystals.

When the solvent is pure THF, NaBr or NaCl crystals pass through the filter paper, and the filtrate is not transparent and causes the filter paper to be clogged finally, thus making filtration or washing of the filter cake to the end difficult. If normal filtration is infeasible, $Bi(OtAm)_3$ contaminated with NaBr or NaCl is liable to bumping, distillation thereof cannot be conducted steadily, and $Bi(OtAm)_3$ recovered by distillation has been contaminated with NaBr or NaCl, thus failing to provide high-purity $Bi(OtAm)_3$.

The yield of $Bi(OtAm)_3$ obtained in Example 1 was 70% or more, and its analysis revealed that the content of Bi was 44.0wt % which almost agreed with the theoretical content of 44.4%, while the content of each of impurities such as Na, K, Mg, Ca and Fe was 1 ppm or less, indicating that this product had high purity.

EXAMPLES

Example 1

The atmosphere in a 5-L four-necked flask equipped with a Dimroth condenser and a stirrer was vacuum-replaced by an Ar gas, and in this flask, 347 g (3.15 mol) NaOtAm was added to and dissolved in 3 L of a mixed organic solvent (10 wt % THF+90 wt % toluene). Separately, the atmosphere in a 2-L eggplant type flask was vacuum-replaced by an Ar gas, and in this flask, 470 g (1.05 mol) $BiBr_3$ was added to 1.5 L of a mixed organic solvent (10 wt % THF+90 wt % toluene), but the $BiBr_3$ could not completely be dissolved in the solvent and a part of the $BiBr_3$ was suspended to form a uniform dispersion. The $BiBr_3$ solution in this 2-L eggplant type flask was added over 20 minutes to the NaOtAm solution in the 5-L four-necked flask. The exothermic reaction proceeded for about 1 hour. After the exothermic reaction was finished, the reaction mixture was aged by stirring it at 80° C. for 6 hours. The solvent at this point consisted of (10 wt % THF+90 wt % toluene). Using filter paper No. 131 set on a funnel of 28 cm in diameter, the reaction mixture was filtered in Ar under reduced pressure at a pressure of 50 Torr. The filtration was finished in 8 hours, to give a transparent filtrate having no violet color. Then, the solvent was distilled away at a pressure of 1 Torr, whereby 440 g of $Bi(OtAm)_3$ was obtained. Then, Bi $(OtAm)_3$ was distilled at 140° C. at 1 Torr to give 374 g (0.795 mol) white $Bi(OtAm)_3$. The overall yield from synthesis to distillation was 76%.

The content of Bi as quantified by ICP emission analysis was 44.0 wt % which almost agreed with the theoretical content of 44.4 wt %, while the content of each of impurities such as Na, K, Mg, Ca and Fe was 1 ppm or less, indicating that this product had high purity. Examples 2 and 3 & Comparative Examples 1, 2 and 3

In Examples 2 and 3 and Comparative Examples 1, 2 and 3, the same procedure as in Example 1 was conducted except that the ratio of the mixed organic solvent was changed.

The results of these examples along with Example 1 are shown in Table 1.

TABLE 1

|  | THF | Toluene | Filtrate | Filtration time | Violet coloration | Yield |
| --- | --- | --- | --- | --- | --- | --- |
| Example 1 | 10 wt % | 90 wt % | Transparent | 8 hours | none | 76% |
| Example 2 | 5 wt % | 95 wt % | Transparent | 7 hours | none | 60% |
| Example 3 | 30 wt % | 70 wt % | Transparent | 10 hours | none | 62% |
| Comparative Example 1 | 100 wt % | 0 wt % | The filtrate was in a suspended state from the start, and the filtration rate was gradually decreased, thus making filtration finally infeasible. |  | present | 40% |
| Comparative Example 2 | 50 wt % | 50 wt % | Turbid | 24 hours | present | 43% |
| Comparative Example 3 | 0 wt % | 100 wt % | Transparent | 8 hours | none | 20% |

As exemplified above, the process of this invention is suitable for mass production of $Bi(OtAm)_3$ and improves the yield because the filtering separation of NaBr formed as a byproduct in the reaction step can be effected easily and reliably in a short time. Further, because of the prevention of contamination with NaBr in the distillation step, high-purity $Bi(OtAm)_3$ can be obtained. Further, because THF is used in a less amount, the deterioration of $Bi(OtAm)_3$ can be prevented.

What is claimed is:

1. A process for producing bismuth tertiary amyloxide, which comprises reacting bismuth bromide or bismuth chloride with sodium tertiary amyloxide or potassium tertiary amyloxide in an organic solvent containing tetrahydrofuran, then separating a byproduct sodium bromide or potassium bromide, or sodium chloride or potassium chloride, by filtration and recovering bismuth tertiary amyloxide by distillation under reduced pressure.

2. The process for producing bismuth tertiary amyloxide according to claim 1, wherein the organic solvent containing tetrahydrofuran is a toluene solution containing 5 to 30 weight % tetrahydrofuran.

* * * * *